US008241901B2

(12) United States Patent
Huang et al.

(10) Patent No.: US 8,241,901 B2
(45) Date of Patent: Aug. 14, 2012

(54) METHOD OF SECRETORY EXPRESSION OF LYSOSTAPHIN IN *ESCHERICHIA COLI* AT HIGH LEVEL

(75) Inventors: Qingshan Huang, Shanghai (CN); Hairong Lu, Shanghai (CN); Wanying Lu, Shanghai (CN)

(73) Assignee: Shanghai Hi-Tech United Bio-Technological Research & Development Co., Ltd., Shanghai (CN)

( * ) Notice: Subject to any disclaimer, the term of this patent is extended or adjusted under 35 U.S.C. 154(b) by 376 days.

(21) Appl. No.: 11/995,735

(22) PCT Filed: Jul. 11, 2006

(86) PCT No.: PCT/CN2006/001640
§ 371 (c)(1),
(2), (4) Date: Jan. 15, 2008

(87) PCT Pub. No.: WO2007/009351
PCT Pub. Date: Jan. 25, 2007

(65) Prior Publication Data
US 2009/0186380 A1 Jul. 23, 2009

(30) Foreign Application Priority Data
Jul. 22, 2005 (CN) .......................... 2005 1 0028038

(51) Int. Cl.
*C12P 21/00* (2006.01)
*A61K 38/00* (2006.01)

(52) U.S. Cl. ........ 435/332; 435/325; 435/335; 435/268; 435/69.7; 435/252.33; 435/69.1; 435/91.4; 435/476; 530/350; 930/300

(58) Field of Classification Search .................. None
See application file for complete search history.

(56) References Cited

U.S. PATENT DOCUMENTS

| 4,931,390 | A |   | 6/1990 | Recsei |  |
|---|---|---|---|---|---|
| 6,132,954 | A | * | 10/2000 | Lupski et al. | 435/4 |
| 2002/0194629 | A1 | * | 12/2002 | Bramley et al. | 800/8 |
| 2004/0110670 | A1 | * | 6/2004 | Arico et al. | 514/12 |
| 2005/0019833 | A1 | * | 1/2005 | Ohkawa et al. | 435/7.1 |

FOREIGN PATENT DOCUMENTS
WO    WO 03082184 A2 * 10/2003

OTHER PUBLICATIONS

Deng et al. (1998) Cloning and high-level expression of plasminogen activator inhibitor-1 cDNA derived from human glomerular mesangial cells, Sci. China Series C: Life Sci., vol. 41, No. 3, pp. 315-322.*
Invitrogen (2009, updated) pBADHisA, www.embl-hamburg.de/~geerlof/webPP/vectordb/bact_vectors/maps_seqs_mcs/pBADHis/pBADHisA_map.pdf, pp. 1-2.*
Huang et al, "Detection of Recombinant Lysostaphin Using Antibody Sandwich Enzyme-Linked Immunoadsorbent Assay (ELISA)", Chinese Journal of Biotechnology, 2007, vol. 23(1), pp. 117-121, published by Elsevier BV.
Blagoev et al., "Inhibition of Adipocyte Differentiation by Resistin-like Molecule α", The Journal of Biological Chemistry. vol. 277, No. 44, Nov. 1, 2002 (pp. 42011-42016).
Ni et al., "Accelerating Whole-Cell Biocatalysis by Reducing Outer Membrane Permeability Barrier", published online at Wiley InterScience (www.interscience.wiley.com), Aug. 19, 2004.
McSweeney et al., "Nuclear Localization of the *Escherichia coli* Cytolethal Distending Toxin CdtB Subunit", Cellular Microbiology (2004), vol. 6, No. 5, pp. 447-458.
Mushtaq et al., "The COOH Terminus of Arylamine N-Acetyltransferase from *Salmonella typhimurium* Controls Enzymic Activity", The Journal of Biological Chemistry, vol. 277, No. 14, Apr. 5, 2002 (pp. 12175-12181).
Invitrogen Manual titled "pBAD/gIII A, B, and C", Copyright 1998-2001, otherwise updated.
McCoy, M., "Killing Staph Together", Chemical & Eng. News, vol. 82, No. 14, pp. 36,38,40 (2004).

* cited by examiner

*Primary Examiner* — Anand Desai
*Assistant Examiner* — Samuel Liu
(74) *Attorney, Agent, or Firm* — Miller, Matthias & Hull LLP

(57) ABSTRACT

A method of secretory expression of lysostaphin in *Escherichia coli* at high level, which comprises constructing a expression vector by cloning a sequence encoding a signal peptide which is suitable for secretory expression in *Escherichia coli* before part or whole gene sequence which encodes mature lysostaphin, and ligating the cloned sequence with a promoter; and transforming *Escherichia coli* with the expression vector, culturing and fermenting, and then isolating lysostaphin from the supernatant of the fermentation broth. The advantage of secretory expression is that the expression product can exist in the medium in an active form, and thus does not need the process for renaturation of the inclusion body; it is more easily to purify from the supernatant of the fermentation broth with high rate of recovery; and there is less contamination from the host's proteins.

14 Claims, 4 Drawing Sheets

Lanes    M    1    2    3    4

Lanes    A    M    B

SEQUENCE LISTING

<160> NUMBER OF SEQ ID NOS: 7

<210> SEQ ID NO 1
<211> LENGTH: 93
<212> TYPE: DNA
<213> ORGANISM: Artificial Sequence
<220> FEATURE:
<223> OTHER INFORMATION: Chemically Synthesized Primer

<400> SEQUENCE: 1
tacatatgaa aaagacagct atcgcgattg cagtggcact ggcaggtttc gctaccgtcg    60
ctcaggctgc tgcaacacat gaacattcag cac                                 93

<210> SEQ ID NO 2
<211> LENGTH: 25
<212> TYPE: DNA
<213> ORGANISM: Artificial Sequence
<220> FEATURE:
<223> OTHER INFORMATION: Chemically Synthesized Primer

<400> SEQUENCE: 2
ccaaagcttc aactttagga atgag                                          25

<210> SEQ ID NO 3
<211> LENGTH: 21
<212> TYPE: PRT
<213> ORGANISM: Artificial Sequence
<220> FEATURE:
<223> OTHER INFORMATION: sig_peptide

<400> SEQUENCE: 3

Met Lys Lys Thr Ala Ile Ala Ile Ala Val Ala Leu Ala Gly Phe Ala
1               5                   10                  15

Thr Val Ala Gln Ala
            20

<210> SEQ ID NO 4
<211> LENGTH: 246
<212> TYPE: PRT
<213> ORGANISM: Artificial Sequence
<220> FEATURE:
<223> OTHER INFORMATION: mat_peptide

<400> SEQUENCE: 4

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

```
Gln Asp Pro Met Pro Phe Leu Lys Ser Ala Gly Tyr Gly Lys Ala Gly
        130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
            180                 185                 190
Val Leu Lys Ala Gly Gln Thr Ile His Tyr Asp Glu Val Met Lys Gln
        195                 200                 205
Asp Gly His Val Trp Val Gly Tyr Thr Gly Asn Ser Gly Gln Arg Ile
    210                 215                 220
Tyr Leu Pro Val Arg Thr Trp Asn Lys Ser Thr Asn Thr Leu Gly Val
225                 230                 235                 240
Leu Trp Gly Thr Ile Lys
                245
```

<210> SEQ ID NO 5
<211> LENGTH: 31
<212> TYPE: PRT
<213> ORGANISM: Artificial Sequence
<220> FEATURE:
<223> OTHER INFORMATION: sig_peptide

<400> SEQUENCE: 5

```
Met Lys Lys Met Ser Leu Phe Gln Asn Met Lys Ser Lys Leu Leu Pro
1               5                   10                  15
Ile Ala Ala Val Ser Val Leu Thr Ala Gly Ile Phe Ala Gly Ala
            20                  25                  30
```

<210> SEQ ID NO 6
<211> LENGTH: 37
<212> TYPE: PRT
<213> ORGANISM: Artificial Sequence
<220> FEATURE:
<223> OTHER INFORMATION: sig_peptide

<400> SEQUENCE: 6

```
Met Lys Lys Thr Lys Asn Asn Tyr Tyr Thr Arg Pro Leu Ala Ile Gly
1               5                   10                  15
Leu Ser Thr Phe Ala Leu Ala Ser Ile Val Tyr Gly Gly Ile Gln Asn
            20                  25                  30
Glu Thr His Ala Ser
        35
```

<210> SEQ ID NO 7
<211> LENGTH: 24
<212> TYPE: PRT
<213> ORGANISM: Artificial Sequence
<220> FEATURE:
<223> OTHER INFORMATION: sig_peptide

<400> SEQUENCE: 7

```
Met Lys Arg Leu Cys Leu Trp Phe Thr Val Phe Ser Leu Phe Leu Val
1               5                   10                  15
Leu Leu Pro Gly Lys Ala Leu Gly
            20
```

METHOD OF SECRETORY EXPRESSION OF LYSOSTAPHIN IN *ESCHERICHIA COLI* AT HIGH LEVEL

This application is a 35 U.S.C. 371 filing of International Application No. PCT/CN2006/001640. The international application claims priority from China Patent Application No. 200510028038.0, filed on Jul. 22, 2005.

BACKGROUND

1. Technical Field

The present invention relates to production of protein or polypeptide drugs using recombinant DNA techniques, and specifically, relates to a method of producing lysostaphin by secretory expression in *Escherichia coli*.

2. Background Art

Lysostaphin was first found by Schindler and Schuhard (U.S. Pat. No. 3,278,378; 1966) in the culture of *Staphylococcus simulans* in 1964, which has a molecular weight of 27 kDa, and consists of 246 amino acids. The lysostaphin, which is an endopeptidase, functions through lysing the pentaglycine cross-links in *Staphylococcus* cell wall peptidoglycan, thereby disrupting the integrity of the cell wall and lysing the bacterial cell body. The lysostaphin gene has been expressed in *Escherichia coli, Bacillus subtitlis* and *Bacillus sphaericus* etc. utilizing molecular cloning method in China and abroad since 1980s. Because of its unique mechanism of killing bacteria, lysostaphin is able to lyse the cell wall of *Staphylococcus* quickly at a low concentration, hence it has an immediate action and a robust activity against the bacteria. In addition, a resistant bacterial strain is rarely induced by lysostaphin, and lysostaphin has a specific antibacterial spectrum. Recombinant lysostaphin in high purity can be commercially manufactured in China and abroad nowadays, and it has been widely used in studies of bacteriology, disinfection, and enzymology, and in clinically anti-bacterial therapy etc.

Since *Staphylococus simulans* belongs to a pathogen and produces only limited amount of lysostaphin, and for sake of the recent development of molecular biology technology, Recsei et al from the U.S.A. utilized the molecular cloning method to express lysostaphin gene in *Escherichia coli* JM 105, *Bacillus subtilis* and *Bacillus sphaericus* in 1987. The amount of lysostaphin expressed in *Escherichia coli* JM 105 is 3 ug/ml, of which 65% exists in the culture supernatant, 15% in the cell periplasm, and 20% in the cytoplasm. A patent was granted in 1990, with the patent No. 4931390, which discloses inserting a 1.5 kb lysostaphin-encoding DNA fragment into vector pUC8, pBC16, pBD64 or pSPV1 to form the recombinant plasmid pRG5, pJP1, pDF8 or pRP1, respectively. pRG5 is used to transform *Escherichia coli* JM105. pJP1, pDF8, and pRP1 are used to transform various *Bacillus* (*Bacillus subtilis* BD170, *Bacillus sphaericus* 00), the lysostaphin produced thereby is identified by immunological techniques and electrophoresis, then compared with lysostaphin produced by *S. simulans*. The amount of lysostaphin (150 mg/L) produced from *Bacillus sphaericus* transformants is 5 times of that produced by *S. simulans*. This referenced patent also provides a 1.5 kb DNA sequence, which encodes a precursor of prolysostaphin with 389 amino acids, and this precursor is processed to be mature lysostaphin after translation. Recently it has been found that lysostaphin has heterogeneous N-terminal, most of them have two amino acids shorter than that of wild-type lysostaphin.

WALTER P. HAMMES et al from Germany expressed the lysostaphin gene with the precursor deleted in Meat Lactobacilli (a *lactobacillus*) in 1996. The aim for deleting the precursor is to acquire stable expression in Meat Lactobacilli, please see patent No.: EP0759473; 1997, but this method remains to be intracellular expression.

In 1999, an Indian company, Biotechnology International Limited applied for a patent relating to recombinant mature lysostaphin, publication No. WO 01/29201, wherein the lysostaphin precursor and the signal peptide portion are deleted, the start codon ATG (encoding the first amino acid: methionine) is added directly before the recombinant mature lysostaphin gene, and the above engineered sequence is cloned into pET11b positioned behind T7 promoter, and then the lysostaphin expression is induced by IPTG. In this referenced patent application, the lysostaphin is expressed in *Escherichia coli* as an inclusion body, with the desired protein stored in the cell as an insoluble inclusion body, and the protein can be only isolated by disrupting the bacterial cell. During the isolation, protein denaturants has to be used, and the protein must be renatured. However, various molecules will incorrectly bind together and form into abnormal structures in the renaturation. At the same time, the cell body remnants are hard to be cleaned out in the genetically-engineered drug manufacturing process, thus negatively affecting the quality of the recombinant product.

There is no highly effective way of secretory expression of the lysostaphin in *Escherichia coli*. Secretory expression has the following advantages: the expressed protein exists in the culture medium as a final active form, so there is no need for renaturation of inclusion body; the desired protein is relatively easy to be isolated from the culture supernatant, with high yield; and there is less contamination of the proteins from host.

SUMMARY OF THE INVENTION

The technical problem, which needs to be solved by the present invention, is to provide a method for highly effective expression of lysostaphin in *Escherichia coli* by means of secretion to overcome the defects in the art.

The general inventive concept of the invention is as follows:

Since the discovery of lysostaphin in 1960 till now, in view of this enzyme's excellent bactericide activity to *Staphylococcus aureus*, in particular, to a drug-resistant strain of *S. aureus*, studies for its medical use in human have been performed at home and abroad, and even have gone to the phase of new drug approval application. However, since the recombinant lysostaphin has only been successfully expressed in *Bacillus sphaericus* ever since, but this engineered bacterial strain has not been approved for drug use till now, and the prokaryotic expression hosts approved for human drugs are *Escherichia coli* and yeast. This is the problem all the research groups in the whole world are facing and trying to solve when they want to apply for new drugs.

Attempt has been made for years to use *Escherichia coli* for expression of the interested enzyme, but has never succeeded. The German scientist in 1997 and the US scientist in 2003 utilized a *lactobacillus* in stead of *Bacillus sphaericus* to express lysostaphin, but *lactobacillus* is not approved for drug use either, hence the problem also exists during new drug application. In addition, the expression by *lactobacillus* is an intracellularly soluble expression while the cost for such an expression is high.

The Indian scientist utilized *Escherichia coli* to express lysostaphin in a form of inclusion body, and the expressed lysostaphin protein was stored in the cell as an insoluble inclusion body. To isolate the protein, the bacterial cell body must be disrupted beforehand. During the isolation process, protein denaturants must be used, and then the protein has to be renatured finally for drug use. However, there will be numerous molecules with abnormal structures formed by erroneous binding in the renaturation. Also the cell body remnant proteins are the material hard to be cleaned out during the manufacture of genetic engineered drugs, thus negatively affecting the quality of the recombinant product.

Till now, there is no breakthrough both at home and abroad in the field of lysostaphin expression system for human drugs, and the same problem exists in industrialization and new drug application. Therefore, if secretory expression of lysostaphin gene in *Escherichia coli* can be achieved, it will expedite the process of applying for a new drug that has the proprietary IP rights in China, and brings enormous economical and social benefits.

The present invention tries to add a segment of signal peptide sequence that induces secretory expression in *Escherichia coli* before the coding sequence of mature lysostaphin, aiming at secretory expression of lysostaphin in *Escherichia coli*. There is no report in the art about secretory expression of lysostaphin in *Escherichia coli* without presence of prolysostaphin.

The technical solution of the present invention will now be described.

The present invention provides a method for secretory expression of lysostaphin in *Escherichia coli*, including the steps of:

(1) Constructing expression vectors, including cloning a signal peptide-encoding sequence before part or whole gene sequence of mature lysostaphin, and linking the above engineered sequence to a promoter;

(2) Transforming *Escherichia coli* with the constructed vector of step (1), and culturing the transformed *Escherichia coli* via fermentation; and (3) Isolating lysostaphin from the supernatant of the fermentation broth.

Wherein the lysostaphin has the same sequence with the wild-type lysostaphin, and its mutants are also included, such as the mutant with two alanine deleted at N-terminus.

Wherein the signal peptide is one of Omp A, phoA, Lysn, pelB.

Amino acid sequence of OmpA signal peptide is below:

SEQ ID NO: 3:   MKKTAIAIAV ALAGFATVAQ A

Amino acid sequence of phoA signal peptide is below:

SEQ ID NO: 5:   MKKMSLFQNM KSKLLPIAAV SVLTAGIFAG A

Amino acid sequence of Lysn signal peptide is below:

SEQ ID NO: 6:
MKKTKNNYYT RPLAIGLSTF ALASIVYGGI QNETHAS

Amino acid sequence of pelB signal peptide is below:

SEQ ID NO: 7:   MKRLCLWFTV FSLFLVLLPG KALG"

Wherein the type of lysostaphin expression in step (2) is inducible expression.

Wherein said vector is an expression vector for *Escherichia coli*, may be selected from one of the pUC series, pET series or pGEX series, or even pBV220.

Wherein the promoter may be selected from one of T7 promoter, P1Pr promoter or lacUV5 promoter.

Particularly, the steps are as follows: first, a pair of suitable primers were synthesized, then the lysostaphin sequence was selectively amplified by PCR method utilizing pyrobest enzyme (a high fidelity DNA polymerase) and whole DNA of *Staphylococus simulans* (NRRL B-2628) as a template. The amplified product was determined and recovered through electrophoresis on agarose containing Ethidium bromide. The purified amplification product was digested with NdeI and HindIII. The digested segment was ligated to the vector digested with NdeI and HindIII in the same way using T4 DNA ligase at 16 degrees C. for 2 hours. The ligation mix was used to transform *Escherichia coli*, thus getting the recombinant plasmid.

The recombinant plasmid was sequenced via automatic DNA sequencer. Its sequence was compared with the known sequence encoding the signal peptide and the mature lysostaphin gene, and the comparison result revealed that these sequences were identical.

*Escherichia coli* was transformed with the recombinant plasmid. Positive clones were picked up, and inoculated into 50 ml LB broth (containing 30 mg/ml kanamycin), and incubated at 37 degrees C. with shaking, till $OD_{600}$ of the culture was 0.6, then IPTG was added to a final concentration of 0.05 mM to induce the expression of interested protein, then continued to culture for 3 hours. The fermentation broth was centrifuged, and then the lysostaphin activity in the supernatant was determined by spectrophotometric assay.

The advantage for the method of the secretory expression of lysostaphin in *Escherichia coli* at high level provided by the present invention lies in that the expression product exists in the culture medium in the form of active mature lysostaphin, while no renaturing steps for inclusion body are needed; it is relatively easy and convenient to purify the interested protein from the culture supernatant, with less protein contaminants from host cell; and the expression product amount may be up to 200-400 mg/L, with the yield over 60%.

Lane M: Standard protein molecular weight Marker.

Figure 2:
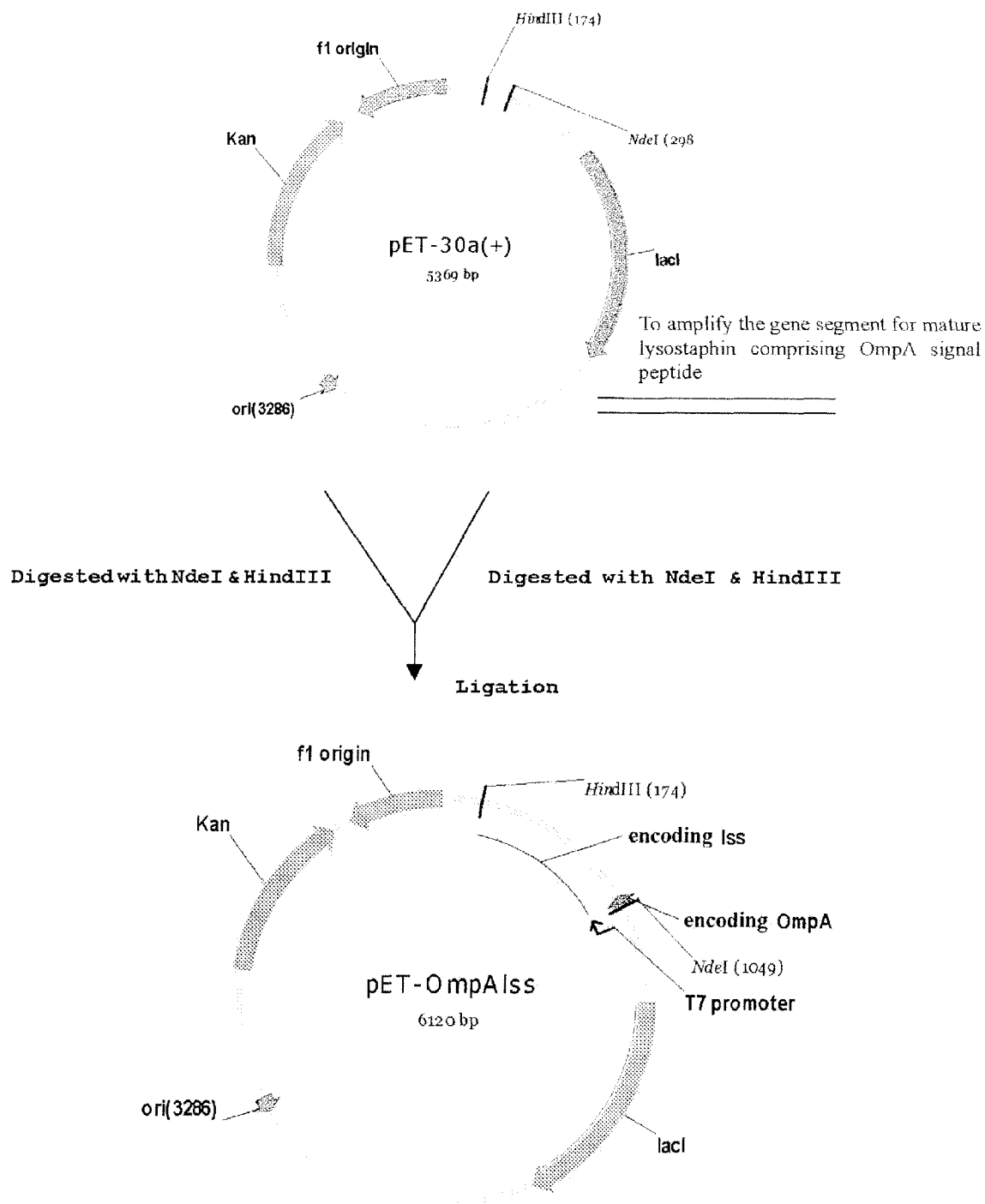

FIG. 2 demonstrates the construction of secretory expression vector for recombinant lysostaphin.

Figure 3:
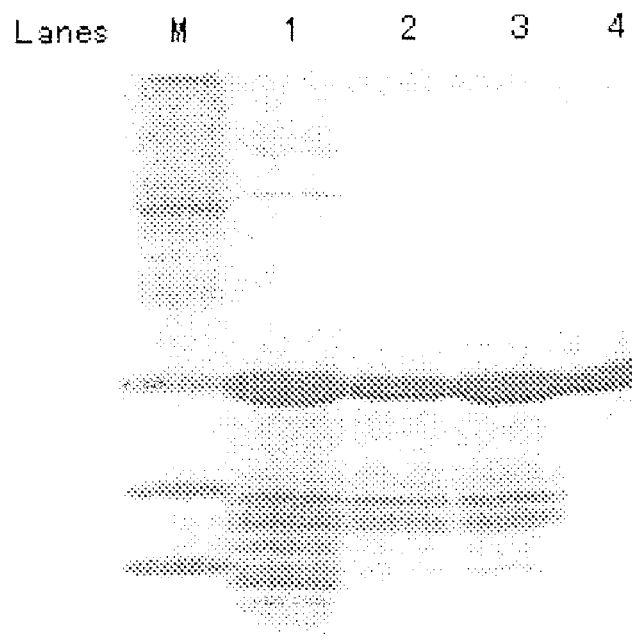

FIG. 3 demonstrates SDS-PAGE electrophoresis of purified lysostaphin.

Figure 4:
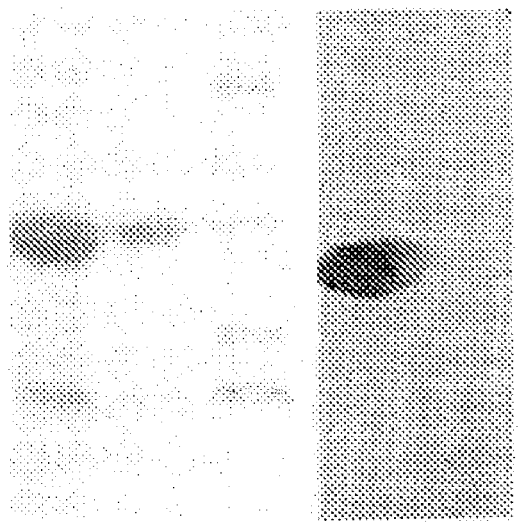

Lane 1: roughly purified sample
Lanes 2-3: further purified sample
Lane 4: refined purification sample
Lane M: standard protein molecular weight Marker FIG. 4 demonstrates SDS-PAGE electrophoresis and Western blot analysis of purified lysostaphin.

Figure 5:
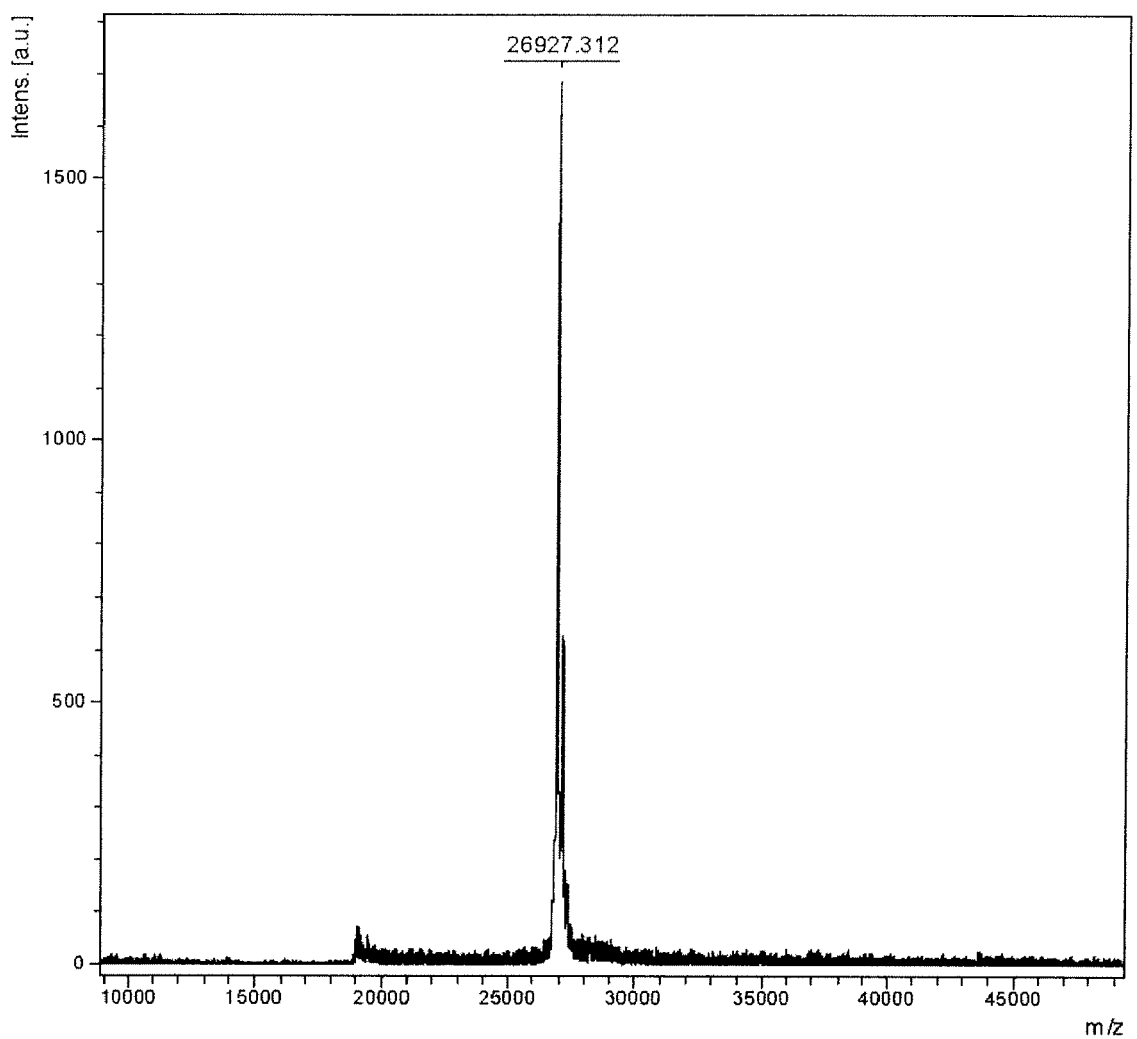

Lane A: SDS-PAGE
Lane B: Western blot
Lane M: standard protein molecular weight Marker;

FIG. 5 demonstrates the purified lysostaphin determined to be of molecular weight 26927Da by matrix-assisted laser desorption/ionization-time-of-flight mass spectrometer (MALDI-TOF).

DETAILED DESCRIPTION OF THE INVENTION

While this invention may be embodied in many forms, there is shown in the drawings and will herein be described in detail one or more embodiments with the understanding that this disclosure is to be considered an exemplification of the principles of the invention and is not intended to limit the invention to the illustrated embodiments.

Specific Mode for Carrying Out the Invention

EXAMPLE 1

Construction of Secretory Expression Vector of Recombinant Lysostaphin, i.e. Cloning of Fusion Gene of the OmpA Signal Peptide and the Mature Lysostaphin First, the oligo-nucleotide sequence was designed and synthesized below:

```
                                            SEQ ID NO: 1
5'-TACAT ATG AAAAAGACAGCTATCGCGATTGCAGTGGCACTGGCAGGT

TTCGCTACCGTCGCTCAGGCTGCTGCAACACATGAACATTCAGCAC-3'

SEQ ID NO: 2
5'-CCA AAGCTT CAACTTTAGGAATGAG-3'
```

In designing SEQ ID NO:1, at 5' terminus was added with a gene sequence of NdeI restriction enzyme site (italic part), as well as a gene sequence encoding OmpA signal peptide (underlined part).

In designing SEQ ID NO: 2, at 5' terminus was added with a gene sequence of HindIII restriction enzyme site (italic part).

Figure 1:
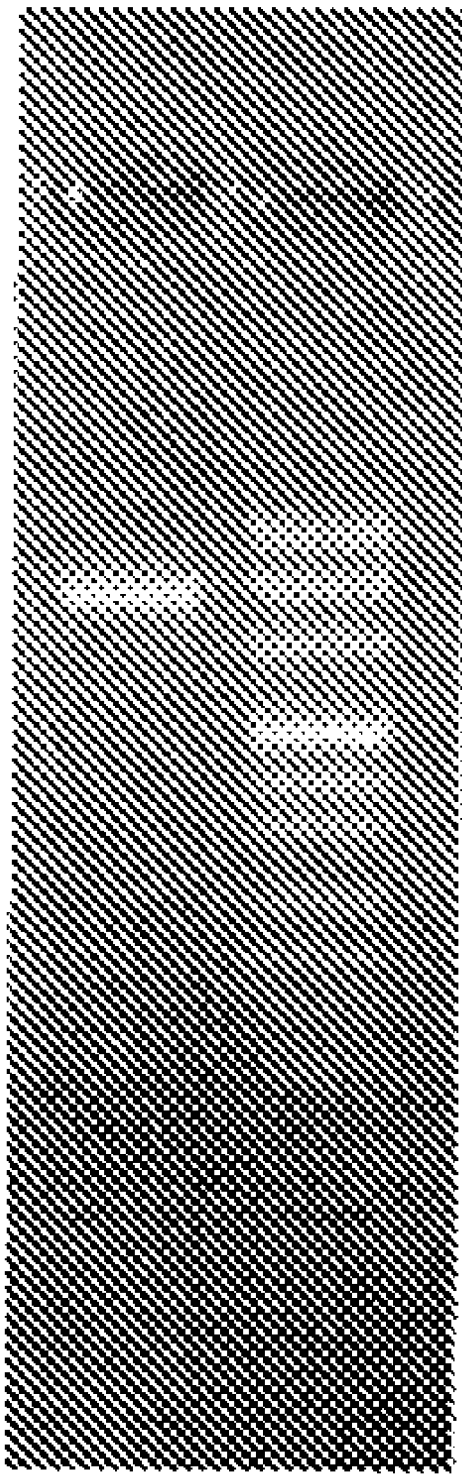
FIG. 1 demonstrates the mature lysostaphin gene amplified by PCR from the whole DNA of *Staphylococus simulans* (NRRL B-2628), Lane 1: a band of amplified product using whole DNA of *Staphylococus simulans* (NRRL B-2628) as a template, SEQ ID NO: 1 and SEQ ID NO: 2 as a pair of primers, size 887bp.

The lysostaphin sequence was selectively amplified through PCR method using pyrobest enzyme (a high fidelity DNA polymerase), and whole DNA of *Staphylococus simulans* (NRRL B-2628) as a template, and SEQ ID NO: 1 and SEQ ID NO: 2 as a pair of primers. The amplified product was determined and recovered by electrophoresis on agarose containing Ethidium bromide. As shown in FIG.1, M denotes a lane of the molecular weight Marker, Lane 1 denotes the band of product sized 887bp, which was amplified using whole DNA of Staphylococus simulans (NRRL B-2628) as a template, and SEQ ID NO: 1 and SEQ ID NO: 2 as a pair of primers.

The purified amplification product was digested with NdeI and HindIII. The digested segment was ligated to the pET30a vector digested with NdeI and HindIII in the same way using T4 DNA ligase at 16 degrees C. for 2 hours. The ligation mix was used to transform *Escherichia coli* DH5a, thus getting the recombinant plasmid pET-OmpAlss, as shown in FIG. 2.

The recombinant plasmid was sequenced via automatic DNA sequencer. Its sequence was compared with the known sequence encoding the signal peptide and the mature lysostaphin gene, and the comparison result revealed that these sequences were identical.

The amino acid sequence encoding OmpA signal peptide of constructed recombinant plasmid pET-OmpAlss is below:

```
    SEQ ID NO: 3:   MKKTAIAIAV ALAGFATVAQ A
```

The amino acid sequence encoding mature lysostaphin of the recombinant plasmid pET-OmpAlss is below:
SEQ ID NO: 4:

```
SEQ. ID. NO: 4:
AATHEHSAQW LNNYKKGYGY GPYPLGINGG MHYGVDFFMN

IGTPVKAISS GKIVEAGWSN YGGGNQIGLI ENDGVHRQWY

MHLSKYNVKV GDYVKAGQII GWSGSTGYST APHLHFQRMV

NSFSNSTAQD PMPFLKSAGY GKAGGTVTPT PNTGWKTNKY

GTLYKSESAS FTPNTDIITR TTGPFRSMPQ SGVLKAGQTI

HYDEVMKQDG HVWVGYTGNS GQRIYLPVRT WNKSTNTLGV

LWGTIK
```

EXAMPLE 2

Establishment of Engineered Bacteria Expressing Recombinant Lysostaphin by Means of Secretion

*Escherichia coli* strains TOP10, JM109(DE3), BL21 (DE3) were transfromed with recombinant plasmid pET-OmpAlss, respectively. Positive clones were picked out and inoculated into 50 ml LB broth (containing 30 mg/ml kanamycin), and incubated at 37 degrees C. with shaking, till $OD_{600}$ of the cultured broth increased to 0.6, then IPTG was added to a final concentration of 0.05 mM to induce protein expression, further incubated for another 3 hours. The fermentation culture was centrifugated, and the lysostaphin activity in the supernatant was determined by spectrophotometric assay.

EXAMPLE 3

Determining Lysostaphin Activity by Spectrophotometric Assay

*Escherichia coli* strains TOP10, JM109(DE3), BL21 (DE3) containing recombinant plasmid pET-OmpAlss of Example 2 were used to determine the lysostaphin activity by spectrophotometric assay. In particular, the determining method is below:

1. Principle

The quantitative assay of lysostaphin is accomplished by spectrophotometric assay, using the coupled KNR light blue dyed *Staphylococcus aureus* cell wall peptidoglycan (KNR-PG) as a color resource substrate. According to the amount of small molecules of soluble segment product carrying the KNR dye moiety that is quantitatively released during the enzyme action process, the supernatant is determined calorimetrically to calculate the activity of the enzyme. This method is easy and convenient, with high sensitivity and visualization.

2. Instruments and Reagents
2.1 Instruments:
2.1.1 Ultra violet—visible spectrophotometer or enzyme-labeled instrument;
2.1.2 high speed freezing desktop centrifuge;
2.1.3 electronic scale;
2.1.4 electronic constant temperature water bath;
2.1.5 10 μl, 20 μl, 200 μl, 1000 μl pipettes and tips;
2.1.6 vortex
2.2 Reagents:

2.2.1 lysostaphin working sample, prepared by the applicant;

2.2.2 color resource substrate KNR-PG prepared by the applicant, homogenously suspended in 0.2 mol/L Gly-NaOH buffer (pH10.0) in a ratio of 1:5 (m/v), for later use;

2.2.3 glycine and NaOH are analytical grade, prepared to be 0.2 mol/L Gly-NaOH buffer, for later use (pH 10.0);

2.2.4 Tris, prepared to be 0.05 mol/L Tris-HCl buffer for later use (pH7.5); 2.2.5 95% ethanol, analytical grade.

3 Experimental Steps 3.1 Preparation of Lysostaphin Working Sample

The lysostaphin working sample is stored at −20 degrees C. after being calibrated. Right before its use, 1.0 ml of 0.05 mol/L Tris-HCl buffer (pH7.5) is precisely added, to make it resolve to get a reference sample of 90.0 U/ml, then aliquoted into several Eppendorf tubes, 50 μl for each tube, and stored at less than −30 degrees C. in a refrigerator. Right before its use, 450 μl of 0.05 mol/L Tris-HCl buffer (pH7.5) is added into one such tube to dilute it into 9.0 U/ml reference solution. Each tube is used once to avoid repeated thawing and freezing.

3.2 Preparation of Standard Curve

Six clean and dry Eppendorf tubes are numbered, and are added with corresponding amount of the lysostaphin reference solution according to the sequence in Table 1, and then are added with various amount of 0.2 mol/L Gly-NaOH buffer.

Then 130 μl of the color resource substrate KNR-PG is added according to the order of numbering, after the substrate is added, each tube is rapidly mixed to homogenize the contents in the tube.

Then the Eppendorf tube containing the above added solution is transferred to 37 degrees C. water bath and incubated for 20 min.

The Eppendorf tube is taken out of the water bath, 300 μl of 95% ethanol is added in the order of numbering to stop the reaction, and centrifuged at 10,000 rpm for 10 min, after centrifugation, the absorbency of the supernatant is determined at 595 nm, with the number 0 tube as a blank control.

The lineal regression curve is plotted according to the determined absorbency value and the corresponding reference sample concentration C (U/ml):

$$A = KC + B$$

wherein K is the standard slope, B is the intercept, A is the absorbency, C is the concentration (U/ml).

TABLE 1

| Preparation of standard curve | | | | | | |
|---|---|---|---|---|---|---|
| Tube number | 0 | 1 | 2 | 3 | 4 | 5 |
| Lysn (μl) | 0 | 20 | 40 | 60 | 80 | 100 |
| Gly buffer (μl) | 770 | 750 | 730 | 710 | 690 | 670 |
| substrate (μl) | 130 | 130 | 130 | 130 | 130 | 130 |
| incubating in 37 degrees C. water bath for 20 min | | | | | | |

TABLE 1-continued

| Preparation of standard curve | | | | | | |
|---|---|---|---|---|---|---|
| Tube number | 0 | 1 | 2 | 3 | 4 | 5 |
| 95% ethanol (μl) | 300 | 300 | 300 | 300 | 300 | 300 |
| Lysn final concentration | 0 | 0.2 | 0.4 | 0.6 | 0.8 | 1.0 |

3.3 Sample Assaying

The assay method is like the method for standard curve. The sample to be assayed is pre-diluted with 0.05 mol/l Tris-HCl dilution buffer (pH7.5), 50 μl is used for assaying, with each sample assayed in duplicate, and the result is the average value of twice measures.

4. Calculation of the Result

Calculation formula:

$$C_0 = N \times C_{measure} \times 0.9/0.05$$

wherein: $C_{measure}$ is the measured value (U/ml) for the sample, N is the dilution times, $C_0$ is the original activity (U/ml) of the sample, 0.9 is the reaction volume (ml), 0.05 is the added sample volume (ml).

5 Results

*Escherichia coli* strains TOP10, JM109 (DE3), BL21 (DE3) containing the recombinant plasmid pET-OmpAlss had a lysostaphin expression activity of 56 U/ml, 45 U/ml, 70 U/ml, respectively.

EXAMPLE 4

Identification of Recombinant Lysostaphin

TOP10 containing recombinant plasmid pET-OmpAlss was inoculated into 50ml LB broth (containing 30mg/ml kanamycin), and incubated at 37° C. for 16 hours with shaking, then re-inoculated into laboratory shake flask with 3 liter LB broth (containing 30mg/ml kanamycin), incubated at 37° C. for 5 hours with shaking, then IPTG was added to a final concentration of 0.05 mM, then further cultured for another 3 hours to induce the expression of the protein; next, the fermentation broth was centrifuged, and purified by a cation column chromatograph, hydrophobic column chromatograph, gel filtration, finally to obtain 83 mg lysostaphin product with purity of greater than 95% and specific activity of 1103 U/mg, which was comparable to the specific activity of lysostaphin from Sigma.

The purified lysostaphin was identified by SDS-PAGE electrophoresis and western blot, as shown in FIG.3 and FIG.4, wherein lanes 1-4 are fermentation supernatant, cation column chromatograph purified sample, hydrophobic chromatograph purified sample, gel filtration purified sample, respectively; and lane M is low molecular weight Marker.

The purified lysostaphin was determined to be of molecular weight 26927 Da by MALDI-TOF (as shown in FIG. 5), very close to the theoretically calculated molecular weight 26924 Da, and to the molecular weight 26912 Da of Sigma lysostaphin.

The N-terminal amino acid residue assay results of the purified lysostaphin: the first 15 amino acids at the N-terminus were identical to those of the mature lysostaphin, i.e., SEQ ID NO: 4.

We claim as our invention:

1. A method for secretory expression of lysostaphin in *Escherichia coli*, characterized by comprising the steps of:
   (1) constructing an expression vector by cloning a DNA sequence encoding a signal peptide before a part or the whole gene sequence of mature lysostaphin polypeptide, and linking thus cloned DNA sequence to a promoter, wherein the signal peptide is phoA, OmpA, Lysn or pelB;
   (2) transforming *Escherichia coli* with the vector constructed in step (1), culturing and fermenting; and
   (3) isolating the lysostaphin polypeptide from the supernatant of said culturing and fermenting which contains said secretorily expressed lysostaphin polypeptide.

2. The method for secretory expression of lysostaphin in *Escherichia coli* according to claim 1, characterized in that the expression of lysostaphin in step (2) is inducible expression.

3. The method for secretory expression of lysostaphin in *Escherichia coli* according to claim 2, characterized in that said vector is a vector for expression in *Escherichia coli*.

4. The method for secretory expression of lysostaphin in *Escherichia coli* according to claim 1, characterized in that said vector is a vector for expression in *Escherichia coli*.

5. The method for secretory expression of lysostaphin in *Escherichia coli* according to claim 4, characterized in that the vector for expression in *Escherichia coli* is one of pUC series, one of pET series or pGEX.

6. The method for secretory expression of lysostaphin in *Escherichia coli* according to claim 4, characterized in that the vector for expression in *Escherichia coli* is pBV220.

7. The method for secretory expression of lysostaphin in *Escherichia coli* according to claim 1, characterized in that said vector is a vector for expression in *Escherichia coli*.

8. An expression vector, comprising a promoter, a DNA sequence encoding a signal peptide, and a part or the whole gene sequence of mature lysostaphin, wherein the DNA sequence encoding a signal peptide is cloned before the part or the whole gene sequence of mature lysostaphin and wherein the signal peptide is phoA, OmpA, Lysn or pelB.

9. The expression vector of claim 8, characterized in that the promoter is one of T7 promoter, P1Pr promoter or lacUV5 promoter.

10. The expression vector of claim 9, characterized in that the vector is one of pUC series, one of pET series or pGEX.

11. The expression vector of claim 8, characterized in that the vector is one of pUC series, one of pET series or pGEX.

12. The expression vector of claim 11, characterized in that the vector is pET-OmpAlss.

13. The expression vector of claim 8, characterized in that said vector is a vector for expression in *Escherichia coli*.

14. The expression vector of claim 13, characterized in that the vector is one of pUC series, one of pET series or pGEX.

* * * * *